United States Patent [19]

Lichtenthaler et al.

[11] Patent Number: 4,618,675

[45] Date of Patent: Oct. 21, 1986

[54] DERIVATIVES AND REDUCTION PRODUCTS OF D-GLUCOPYRANOSYL-ALPHA(1→5)-D-ARABINONIC ACID; AND PRODUCTION OF SAME

[75] Inventors: Frieder W. Lichtenthaler, Mühltal; Roger G. Klimesch, Alsbach-Hahnlein, both of Fed. Rep. of Germany

[73] Assignee: Suddeutsche Zucker-Aktiengesellschaft, Mannheim, Fed. Rep. of Germany

[21] Appl. No.: 562,135

[22] Filed: Dec. 16, 1983

[30] Foreign Application Priority Data

Dec. 28, 1982 [DE] Fed. Rep. of Germany ....... 3248404

[51] Int. Cl.$^4$ ............................................ C07H 15/04
[52] U.S. Cl. ..................................... 536/17.2; 536/4.1; 536/124
[58] Field of Search ......................... 536/4.1, 124, 17.2

[56] References Cited

U.S. PATENT DOCUMENTS 2,190,377  2/1940  Dalmer et al. .
3,565,885  10/1968  Molotsky et al. ................. 536/18.6
4,117,173  9/1978  Schiweck et al. .................... 536/4.1
4,322,523  3/1982  Wagner ............................... 536/4.1

FOREIGN PATENT DOCUMENTS 0130512  10/1979  Japan ..................................... 536/4.1

OTHER PUBLICATIONS

Stanek et al., The Monosaccharides, 1963, pp. 138–141.
Pigman, The Carbohydrates, 1957, p. 148.

Migrdichian, *Organic Synthesis*, vol. 1, 1957, pp. 9–10, 30, 162 and 311 & 322.
"The Monosaccharides", in *Academic Press*, New York, pp. 138ff., 1963.
Dubourg et al, "Oxidation des Hexoses Reducteurs par l'Oxygene en Milieu Alcalin", in *Bull. Soc. Chim. Fr.*, pp. 1353ff., 1959.

Primary Examiner—Johnnie R. Brown
Assistant Examiner—Elli Peselev
Attorney, Agent, or Firm—Armstrong, Nikaido, Marmelstein & Kubovcik

[57] ABSTRACT

The invention relates to derivatives and reduction products of D-glucopyranosyl-alpha(1→5)-d-arabinonic acid, having the general formula:

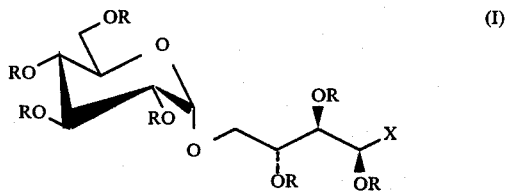

wherein X is one of the following groups: —COOM, —COOR', CONH$_2$ or —CH$_2$OH, where M is an alkali metal and R' is an alkyl group; and where R is a hydrogen atom or an acyl group. The compounds of formula (I) include compounds in which the arabinonic acid chain is closed in a lactone ring.

A method for producing the derivatives and reaction products is described, and uses therefor are also provided.

19 Claims, No Drawings

DERIVATIVES AND REDUCTION PRODUCTS OF D-GLUCOPYRANOSYL-ALPHA(1→5)-D-ARABINONIC ACID; AND PRODUCTION OF SAME

SUMMARY OF THE INVENTION

The present invention relates to derivatives and reduction products of D-glucopyranosyl-alpha(1→5)-D-arabinonic acid, having the general formula:

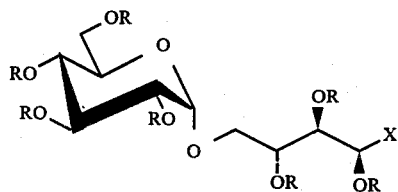

wherein X is one of the following groups: —COOM, —COOR', —CONH$_2$, —CH$_2$OH. and M is an alkali metal and R' is an alkyl group; and wherein R is a hydrogen or acyl group, such as acetyl or benzoyl. The above-described arabinonic acid may also be closed to form a lactone ring.

The present invention also provides a method for producing compounds of formula (I) and includes uses for such compounds.

DETAILED DESCRIPTION

The present invention relates to derivatives and reduction products of D-glucopyranosyl-alpha (1→5)-D-arabinonic acid (hereinafter referred to as "GPAA"), which correspond to the general formula:

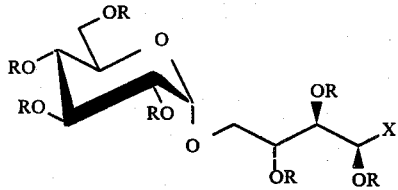

wherein X is one of the following groups: —COOM, —COOR', —CONH$_2$, or —CH$_2$OH, and M is an alkali metal and R' is an alkyl group and may have 1 to 20 carbon atoms; and wherein R is a hydrogen atom or an acyl group and may have 1 to 20 carbon atoms such as acetyl or benzoyl. The arabinonic acid may also be closed to form a lactone ring. The derivatives of the arabinonic acid include, among others, the alkali salts, the alkyl esters, the amide, and the lactone of "GPAA", and D-glucopyranosyl-alpha(1→5)-D-arabinitol (its alcohol reduction product hereinafter referred to as "GPA alcohol").

The derivatives of "GPAA" corresponding to the general formula (I) are novel compounds. They have engineering applications which include their use as intermediate products in chemical syntheses, e.g. in the manufacture of surfactants. The above-mentioned "GPA alcohol", as a result of its sweetness, can be used in solid or liquid form as a sugar substitute, particularly for diabetics and obese persons. As such, the compound may be mixed with other artificial sweeteners or with nutritive carbohydrates which have sweetening value.

The starting material for the manufacture of the compounds with the above general formula is isomaltulose, i.e., D-glucopyranosyl-alpha(1→6)-D-fructose (formula (1) below), which is converted to alkali salts of "GPAA" by air or oxygen oxidation in an alkali solution, which salts may in turn be converted to the corresponding esters, the amide, and the gamma-lactone, by esterification, amidation, or treatment with an acid ring-closing media, respectively. The "GPA alcohol" is obtained from one of the above-mentioned alkyl esters, the above-mentioned lactone, or O-acylation products of any of said esters or said lactone, by specific reduction steps.

The said O-acyl derivatives, particularly the O-acetyl and O-benzyl derivatives of the above-mentioned "GPAA" derivatives, may be obtained from the respective non-O-acylated derivatives by treating with an appropriate acylating agents in an anydrous organic solvents.

The following reaction scheme shows the course of the mentioned reactions, and the structural formulas of the products in the scheme:

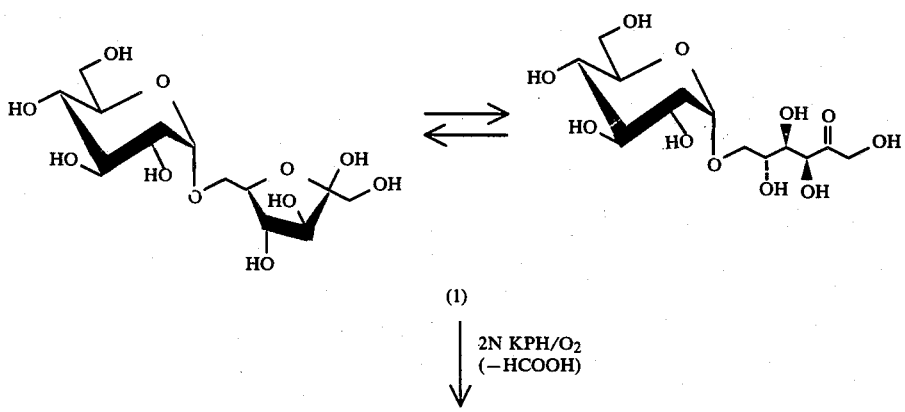

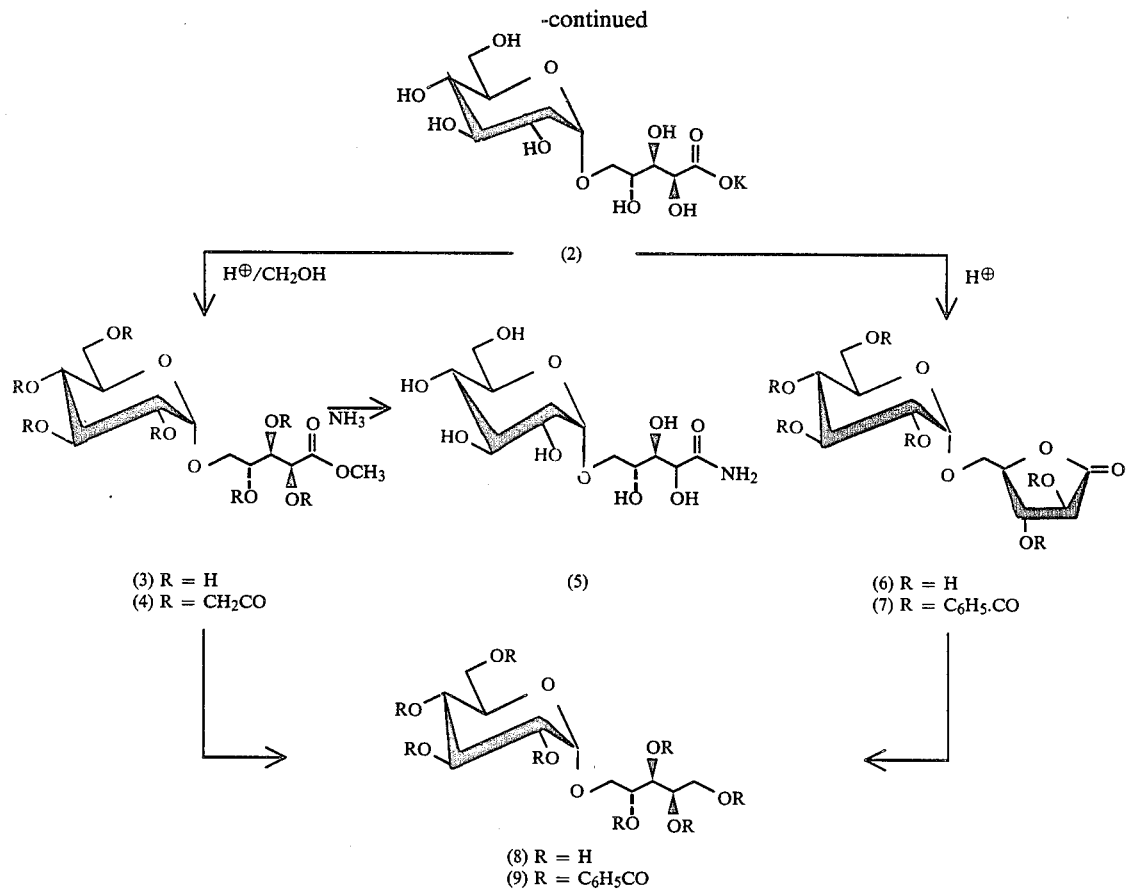

(3) R = H
(4) R = CH₂CO (5)

(6) R = H
(7) R = C₆H₅.CO (8) R = H
(9) R = C₆H₅CO

Methods of oxidation of reducing sugars (e.g., hexoses or pentoses) in alkali metal using pure oxygen or air are discussed by Stanek, J., M. Cerny, J. Kocourek, and J. Pacak, 1963, in "The Monosaccharides", Academic Press, New York, pp. 138 ff., and literature cited therein; these methods produce the salt of the aldonic acid, which has one less carbon atom than the starting material. In the case of the ketohexoses, the reaction appears to take a more complex course. Thus, from L-sorbose, there is obtained, in addition to L-xylonic acid, a significant amount of 2-keto-L-gulonic acid (as disclosed in U.S. Pat. No. 2,190,377); and D-fructose yields other oxidation products in addition to D-arabinonate and formic acid, including glycolic acid, glyceric acid, erythronic acid, and lactic acid, as shown in the data in Bull. Soc. Chim. Fr., 1959: 1353 ff.

In contrast to these reactions which include substantial degradation, the air oxidation of isomaltulose (formula (1) above) according to the present invention, proceeds extremely smoothly and free of any problems to form "GPAA" potassium salt (formula (2) above); by reacting a 5 to 20% solution of isomaltulose with air in 2N KOH solution at room temperature, which may include, for example, strong stirring of the solution or bubbling of air or oxygen through the solution.

The "GPAA" formed is isolated in the form of its potassium salt, by neutralization of the excess KOH with a carboxylic acid or mineral acid, and crystallized from the reaction mixture by addition of methanol.

Yields of the formula (2) product are invariably over 90% (e.g., 96% in Example 1 below), and in some cases are nearly 100%. Apart from the formic acid which is necessarily formed in a 1:1 ratio, there are almost no other oxidation products present in the reaction mixture, although glycosyl-alpha(1→4)-erythronic acid and glycosyl-alpha(1→3)-glyceric acid would have been expected on the basis of the analogy with fructose oxidation. In chromatograms produced at high concentration, traces (under 0.5%) of other unidentified products may be detected.

The preparation of derivatives of "GPAA" such as the methyl ester (formula (3) above) and the lactone (formula (6)) is achievable at only moderate yields under ordinary conditions (in mineral acid and methanol, or aqueous mineral acid), since the glycoside bond is acid unstable, and there is partial degradation to glucose and D-arabinitol (the alcohol derivative of D-arabinonic acid). However, if an acid ion exchange medium is used under specific conditions, there may achieve yields of 85% and 74%, respectively, in these preparations (see Examples 2 and 6, below).

The methyl ester of "GPAA" (formula (3)) may be converted to crystallized "GPAA" amide (formula (5)) in nearly a 100% yield by treating with methanolic ammonia.

The reduction of the "GPAA" methyl ester (formula (3)) or the heptaacetate of the latter (formula (4)) by complex metal hydrides such as NaBH₄ or LiAlH₄, or by atomic hydrogen, yields "GPA alcohol" (formula (8)). This "GPA alcohol" can be characterized by crystalline form with a melting point 156°-158° C. and $[\alpha]_D^{20} = +98.5°$ (c=1, water) and/or may be produced in the form of the octabenzoate (formula (9)).

In a similar manner to the "GPAA" methyl ester, the "GPAA" lactone (formula (6)) or the hexabenzoate of the latter provides yields of over 85% of "GPA alcohol" (formula (8)) upon reduction of the carboxyl group.

All the novel (first synthesized) compounds, namely the products of formula (2) through (9), were characterized microanalytically and chromatographically as pure substances. Their compositions and structures were verified unambiguously by 300 MHz $^1$H nmr spectra with the aid of $^{13}$C nmr and mass spectrographic data.

In a comparative taste test with 10 to 15 people, the sweetness of "GPA alcohol" was determined to be 45% that of saccharin. The sweetness was determined in a triangular test, in comparison to 7–8% aqueous saccharin solutions and in comparison to glucopyranosyl-alpha(1→6)-D-mannitol.

In order to enhance the sweetness of "GPA alcohol" to the level of sweetness of saccharin or greater, "GPA alcohol" may be mixed or "instantized" (i.e., packaged, encapsulated, or the like, so as to mix when dissolved) in solid form with another artificial sweetener, e.g., benzoic acid sulfimide, cyclohexanesulfamate, or phenylalaninylasparaginic acid methyl ester. Solutions of "GPA alcohol" with sweetness enhanced by the addition of other aritifical sweeteners thereto may be dried in mixed form, for example, by spray drying, drum drying, or freeze drying; or they may be used directly.

Also, according to the present invention "GPA alcohol" may be employed in solid or liquid form mixed with other nutritive carbohydrate sweeteners, e.g., fructose, xylitol, or sorbitol, in order to provide a mixture having a sweetness approximate that of saccharin (In the case of fructose, the weight ratio of "GPA alcohol" to fructose in the mixture for this purpose is 1:1). The "GPA alcohol" may be used alone or in mixed sweeteners in place of normal sugar (beet or cane sugar), in home cooking and drink preparation (e.g., in baking, canning, and Jello mold making) as well as in industrial preparation of foods, condiments, confections, drinks, etc. The properties of "GPA alcohol" (e.g., sweetening power, mixability, dryability, classification as a basically natural substance, etc.) make it suitable for use as a sugar substitute, particularly for diabetics and obese persons.

The invention will be explained in more detail hereinafter, with the aid of the following examples which in no way limit the present invention:

EXAMPLE 1

Preparation of "GPAA" potassium salt (formula (2))

A solution of 35.0 g (102.3 mmol) isomaltulose (formula (1)) in 100 ml water is mixed with a solution of 20 g KOH in another 100 ml water, and the mixture is oxidized in a stream of air or oxygen for 8 to 16 hr. For improved mixing of the oxygen with the aqueous solution, a 16,000 rpm turbine is employed. After completion of the reaction, the solution is brought to a pH of 7.5 by careful addition of an acid (e.g., acetic) or by stirring a strongly acidic ion exchange medium, such as Amberlite IR-120, H+-form, into the solution; and then the resulting mixture is concentrated to a syrup, which is then crystallized by treatment with methanol. Recrystallization from 2.5 methanol yields 36.0 g "GPAA" potassium salt (formula (2)) (96% yield in the form of colorless needles, m.p. 172°–174° C., $[\alpha]_D^{20} = +87.8°$ (c=1, water).

$^1$H-NMR (300 MHz, D$_2$O): δ=3.42 (t, 1H, 4'-H), 3.58 (dd, 1H, 2'-H), 3.62–4.04 (m, 9H, 2-H, 3-H, 4-H, 5-H$_2$, 3'-H, 5'-H, 6'-H$_2$), 4.97 (d, 1H, 1'H), $J_{1',2'}=3.5$, $J_{2',3'}=J_{3',4'}=J_{4',5'}=9.5$ Hz.

$^{13}$C-NMR (75 MHz, D$_2$O): δ=61.41 (t, C-6'), 69.42 (t, C-5), 70.36 (d, C-4'), 70.50 (d, C-4), 72.37 (d, C-2'), 72.43 (d, C-2), 72.63 (d, C-3 and C-5'), 73.98 (d, C-3'), 98.98 (d, C-1'), 179.98 (s, C-1).

MS (FC): m/e=405 (100%, M++K).

C$_{11}$H$_{19}$O$_{11}$K.H$_2$O(384.4) Theoretical (%): C 34.37; H 5.51; Found 34.35; H 5.45.

EXAMPLE 2

Preparation of "GPAA" methyl ester (formula (3))

In a 1 liter three-neck flask equipped with stirrer and drying tube, 10.0 g (27.3 mmol) "GPAA" potassium salt (formula (2)), product of Example 1, above) is suspended in 600 ml absolute methanol. To this is added 4 ml of orthoformic acid trimethyl ester and 20.0 g of strongly acidic ion exchange medium (Amberlite IR-120 H+-form) which has been thoroughly washed with water, followed by washing with methanol, and then dried in vacuum over a 75° C. bath. The resulting mixture is reacted until no starting material is detected chromatographically in samples; the time of reaction is about 3 days. The ion exchange medium is then filtered out, the volume of the filtrate solution is reduced concentration by evaporation to about 150 ml, and the resulting supersaturated solution is kept overnight at 5° C. The crystals obtained are deliquefied by suction filtration and washed thoroughly with cold methanol. The yield is 7.95 g (85% yield) GPAA methyl ester, in the form of colorless needles, m.p. 178°–179° C., $[\alpha]_D^{20} = +105.0°$ (c=1, water)

$^1$H-NMR (300 MHz, D$_2$O): δ=3.43 (t, 1H, 4'-H), 3.58 (dd, 1H, 2'-H), 3.64–3.79 (m, 4H, 5-H$_2$, 3'-H), 3.81 (s, 3H, OCH$_3$), 3.83–3.99 (m, 3H, 5'-H, 6'-H$_2$), $J_{2,3}=1.8$, $J_{3,4}=9.4$, $J_{1',2'}=3.7$, $J_{2',3'}=9.8$, $J_{3',4'}=9.4$ Hz.

$^{13}$C-NMR (75 MHz, D$_2$O); δ=53.60 (q, CH$_3$), 61.38 (t, C-6'), 69.25 (t, C-5), 69.59 (d, C-4), 70.41 (d, C-4'), 71.57 (d, C-2), 72.29 (d, C-2'), 72.38 (d, C-5'), 72.62 (d, C-3), 73.95 (d, C-3'), 99.07 (d, C-1'), 176.01 (s, C-1).

MS (FD): M+e=343 (100%, M++1), 311 (45%, M—CH$_3$OH)++1).

C$_{12}$H$_{22}$O$_{11}$ (342.3) Theoretical (%): C 42.10; H 6.48; Found: C 42.11; H 6.40.

EXAMPLE 3

Preparation of 2,3,4,6-tetra-O-acetyl-D-glucopyranosyl-alpha(1→5)-methyl-2,3,4-tri-O-acetyl-D-arabinonate (hepta-O-acetayl "GPAA" methyl ester) (formula (4))

In a 100 ml three-neck flask with stirrer, dropping tunnel and air drying tube, 1.6 g (4.67 mmol) "GPAA" methyl ester (Formula (3)) is dissolved in 25 ml absolute pyridine, and 16 ml acetic anhydride is gradually added thereto at 0° C. over the course of 30 min. The reaction mixture is then allowed to stand for 18 hours at room temperature, and then it is added to 150 ml ice water while stirring, and thereafter, the reaction products are extracted with dichloromethane (3×75 ml). The extracts are successively combined and washed with 2N HCl, saturated NaHCO$_3$ solution, and water; and then the reactants are dried (with Na$_2$SO$_4$), and concentrated by vacuum evaporation to yield the heptaacetyl derivative (formula (4)) in the form of a syrup which does not crystallize. The yield is quantitative (2.96 g), $[\alpha]_D^{24} = +110.8°$ (c=1, CHCl$_3$).

¹H-NMR (300 MHz, CDCl₃): δ=um 2.0 (7s, 21H, 7 Acetyl-CH₃), 3.68 (dd, 1H, 5-H$_a$), 3.75 (dd, 1H, 5-H$_b$), 3.76 (s, 3H, OCH₃), 3.98 (ddd, 1H, 5'-H), 4.08 (dd, 1H, 6-H$_a$) 4.25 (dd, 1H, 6'-H$_b$), 4.85 (dd, 1H, 2'-H), 5.05 (dd, 1H, 4'-H), 5.10 (d, 1H, 1'-H), 5.20 (ddd, 1H, 4-H), 5.30 (d, 1H, 2-H), 5.44 (dd, 1H, 3'-H), 5.63 (dd, 1H, 3-H); $J_{2,3}=2.2$, $J_{3,4}=8.9$, $J_{4,5a}=5.3$, $J_{4,5b}=3.6$, $J_{5a,5b}=11.6$, $J_{1',2'}=3.7$, $J_{2',3'}=10.2$, $J_{3',4'}=9.5$, $J_{4',5'}=10.2$, $J_{5',6'a}=4.4$, $J_{5',6'b}=2.3$, $J_{6'a,6'b}=12.4$ Hz.

MD (FD): m/e=637 (100% M⁺+1).

C₂₆H₃₆O₁₈ (636.6) Calculated theoretical (%): C 49.06; H 5.70; Found C 48.94; H 5.65.

EXAMPLE 4

Preparation of "GPAA" amide (formula (5))

Anhydrous ammonia is introduced into a solution of 2.0 g (5.9 mmol) "GPAA" methyl ester (formula (3), the product of Example 2, supra), in 16 ml methanol, at 0° C., until saturation with ammonia occurs. After 1.5 hr at 0° C., the reaction mixture is allowed to come to room temperature, and then it is concentrated by vacuum evaporation to remove the solvent. The resulting syrupy residue is recrystallized from 35 ml absolute methanol, to yield 1.9 g (98% yield) of the amide of formula (5), in the form of colorless needles, m.p. 170° C. (with decomposition), $[\alpha]_D^{20}=75.0°$ (c=1, water).

¹H-NMR (300 MHz, D₆-DMSO): δ=3.05–3.18 (m, 2H, 2'-H, H'-H), 3.37–3.69 (m, 7H, 4-H, 5-H₂, 3'-H, 5'-H, 6'-H₂), 3.72 (dd, 1H, 3-H), 4.10 (d, 1H, 2-H), 4.38 (s, 1H, OH), 4.4 (d, 1H, OH), 4.59 (d, 1H, OH), 4.65 (d, 2H, 1'-H, OH), 4.77 (d, 1H, OH), 4.83 (d, 1H, OH), 5.14 (d, 1H, OH), 7.14 (d, 2H, NH₂); $J_{2,OH-2}=6.1$, $J_{3,OH-3}=5.0$, $J_{2,3}=0$, $J_{3,4}=10.1$, $J_{1',2'}=3.7$, $J_{NH2\ (gem)}=18.9$ Hz.

MS (FD): m/e=328 (100%, M⁺+1), 311 (40%, M—NH₂)⁺+1).

C₁₁H₂₁N₁O₁₀ (327.3) Ber. (%): C 40.37; H 6.47; N 4.28; Gef. C 40.28; H 6.46; N 4.21.

EXAMPLE 5

Preparation of GPAA gamma-lactone (formula (6))

In a 100 ml two-neck flast, 2.0 g (1.37 mmol) "GPAA" potassium salt (formula (2), the product of Example 1 above, is dissolved in 25 ml water with stirring, 4.0 g of a strongly acidic ion exchange medium (Amberlite IR-120, H⁺-form) which has been successively washed with water and then methanol is added. The resulting mixture is stirred 12 hours at 75° C. After filtration and vacuum concentration, a chromatographically uniform syrup is obtained, which is then purified by elution on a kieselgel column (100 g) with 16:1 acetone:water, to yield 1.25 g (74% yield) of the lactone of Formula (6), with $[\alpha]_D^{20}=+92.5°$ (c=1, water).

¹H-NMR (60 MHZ, D₂O): δ=3.4–4.3 (m, 11H, 2-H, 3-H, 4-H, 5-H₂, 2'-H, 3'-H, 4'-H, 5'-H, 6'-H₂), 4.90 (d, 1H, 1'-H); $J_{1',2'}=3.4$ Hz.

MS (FD): m/e=311 (100%, M⁺+1).

C₁₁H₁₈O₁₀ (310.3) Theoretical (%): 42.58; H 5.85; Found C 42.49; H 5.80.

EXAMPLE 6

Preparation of 5-O-(2,3,4,6-tetra-O-benzoyl-alpha (1→5)-D-glucopyranosyl)-2,3-di-O-benzoyl-D-arabinonic acid gamma-lactone, hexa-O-benzoyl "GPAA" gamma-lactone) (formula (7))

In a 100 ml three-neck flask equipped with a stirrer, a dropping funnel, and a drying tube; 700 mg (2.26 mmol)

"GPAA" gamma-lactone (formula (6)) is dissolved in 12 ml absolute pyridine, and the solution is cooled to 0° C. Freshly distilled benzoyl chloride is added in the amount of 5 ml, and the mixture is allowed to react overnight. The resulting mixture is subjected to hydrolysis and extraction with dichloromethane (3×40 ml). This is followed by successive washing of the combined organic extract phase with 2N HCl, water, saturated NaHCO₃ solution, and water again, then drying with Na₂SO₄, and thereafter the resulting extrast is vacuum evaporation concentrated. This yields a syrup which is purified over kieselgel by elution (i.e., chromatographically) with 40:1 dichloromethane:ethyl acetate, to yield 1.8 g (75% yield) of the hexabenzoate of formula (7)), in the form of a colorless syrup with $[\alpha]_D^{20}=+22.8°$ (c=1, CHCl₃).

¹H-NMR (300 MHz, CDCl₃): δ=4.00 (dd, 1H, 5a-H), 4.33 (dd, 1H, 5b-H), 4.55 (dd, 1H, 6'a-H), 4.66–4.78 (m, 3H, 4-H, 5'-H, 6'b-H), 5.44 (d, 1H, 1'-H), 5.45 (dd, 1H, 2'-H), 5.77 (t, 1H, 4'-H), 6.04 (t, 1H, 3-H), 6.14 (d, 1H, 2-H), 6.28 (dd, 1H, 3'-H), 7.2–7.6 (m, 18H, o- and p-C₆H₅), 7.8–8.2 (m, 12H, m-C₆H₅); $J_{2,3}=7.1$ Hz, $J_{3,4}=6.8$ Hz, $J_{4,5}=2.1$ Hz, $J_{4,5b}=4.8$ Hz, $J_{5a'5b}=11.4$ Hz, $J_{1',2'}=3.7$ Hz, $J_{2',3'}=9.6$ Hz, $J_{3',4'}=9.7$ Hz, $J_{4',5'}=9.9$ Hz, $J_{5',6a}=4.9$ Hz, $J_{6'a,6'b}=12.5$ Hz.

MS (FD): m/e 935 (100%, M⁺+1).

C₅₃H₄₂O₁₆ (934.9) Theoretical (%): C 68.09; H 4.53; Found: C 67.89; H 4.48.

EXAMPLE 7

Preparation of "GPA alcohol" (formula (8))

Boric acid in the amount of 0.5 g is stripped into a solution of 6.85 g (10 mmol) "GPAA" methyl ester (formula (3), the product of Example 2 above) in 250 ml water. Then, 70 ml of a strongly acidic ion exchange medium (Amberlite IR-120, H⁺-form) is added while stirring, and the mixture is cooled to 0° C. A solution of 7.5 g NaBH₄ in 400 ml water is added dropwise to the mixture over 1 hour, with stirring and cooling, and stirring is continued for 1 hour after the addition is completed. The solution is brought to a pH of 9-10 by careful addition of 2N NaOH. The resulting mixture is filtered, the filtrate is passed over a column of ion exchange resin (Amberlite IR-120, H⁺-Form), washed with water (2 liters), and the eluates are combined and concentrated by vacuum evaporation to a volume of 100 ml. A strongly basic ion exchange medium is added and the mixture is stirred 30 minutes to remove any remaining boric acid, filtered, mixed briefly with "Amberlite IR-120" while stirring, filtered again, and then concentrated by vacuum evporation to yield a syrup which, when dissolved in methanol, there is crystallized 5.1 g (81% yield) of "GPA alcohol" (Formula (8)), m.p. 156°–158° C., $[\alpha]_D^{20}=+98.5°$ (c=1, water).

¹H-NMR (300 MHz, D₂O): δ=3.43 (t, 1H, 4'-H), 3.58 (dd, 1H, 2'-H), 3.6–4.0 (m, 11H, 1-H₂, 2-H, 3-H, 4-H, 5-H₂, 3'-H, 5'-H, 6'-H₂), 4.95 (d, 1H, 1'H); $J_{1',2'}=3.5$ Hz, $J_{2',3'}=9.6$ Hz, $J_{3',4'}=J_{4',5'}=9.5$ Hz.

¹³C-NMR (75 MHz, D₂O): δ=61.40 (t, C-6'), 63.95 (t, C-1), 69.44 (t, C-5), 70.09 (d, C-2), 70.44 (d, C-4'), 70.90 (d, C-3), 71.05 (d, C-4), 72.36 (d, C-2'), 72.61 (d, C-5'), 73.97 (d, C-3'), 98.99 (d, C-1').

MS (FD): m/e=337 (100%, M⁺+Na), 315 (80%, M⁺+1).

C₁₁H₂₂O₁₀ (314.3) Ber. (%): C 42.03; H 7.06; Gef. C 41.89; H 7.00.

EXAMPLE 8

Preparation of "GPA alcohol" octabenzoate (formula (9))

In a 250 ml three-neck flask with a stirrer, 3.5 g (10 mmol) "GPAA" methyl ester (formula (3), the product of Example 2 above) is dissolved in 70 ml water, 1.4 g (37 mmol) NaBH$_4$ is added, and the reaction mixture is allowed to stand 2 hr at room temperature. The residual NaBH$_4$ is decomposed by addition of 4.2 ml acetone, the resulting product is deionized by treatment with Amberlite "IR-120" ion exchange resin (H$^+$-Form), and then subjected to filtration. The filtrate is concentrated by vacuum evaporation to 2.9 g of a syrupy mass, and is then benzoylated by treatment with 32 ml benzoyl chloride in 50 ml pyridine for 16 hours at room temperature. The reaction mixture is then stirred into ice water, and extracted with dichloromethane (3×100 ml). The organic extract phases are combined and successively washed with 2N HCl, saturated NaHCO$_3$ solution, and water, which is followed by drying with Na$_2$SO$_4$, and vacuum evaporation to remove all volatiles, leaving a syrup which is then purified (chromatographically) by elution over a silica gel column (500 g) with 40:1 dichloromethane: ethyl acetate, yielding 8.5 g (75% yield) of the octabenzoate of formula (9), in the form of a chromatographically uniform, colorless syrup with $[\alpha]_D^{24} = +79.5°$ (c=1, CHCl$_3$).

$^1$H-NMR (300 MHz, CDCl$_3$): δ=3.92 (dd, 1H, 5-H$_a$), 4.10-4.28 (m, 4H, 5-H$_b$, 5'-H, 6'-H$_2$), 4.61 (dd, 1H, 1-H$_a$), 4.67 (dd, 1H, 1-H$_b$), 5.32 (dd, 1H, 2'H), 5.38 (d, 1H, 1'-H), 5.64 (t, 1H, 4'-H), 5.74 (ddd, 1H, 4-H), 5.95 (ddd, 1H, 2-H), 6.27 (t, 1H, 3'-H), 6.31 (dd, 1H, 3-H), 7.1–7.6 (m, 24H, o- and p-C$_6$H$_5$), 7.7–8.2 (m, 16H, m-C$_6$H$_5$), $J_{1a,1b}$=11.9, $J_{1a,2}$=6.9, $J_{1b,2}$=$J_{5a,5b}$=11.5, $J_{1',2'}$=3.7, $J_{2',3'}$=10.2, $J_{3'4'}$=9.7 Hz.

MS (FD): m/e = 1146 (100%, M+).

C$_{67}$H$_{54}$O$_{18}$ (1147.1) Theoretical (%): C 70.15; H 4.75; Found: C 69.96; H 4.69.

Treatment of the octabenzoate (9) with sodium methoxide with methanol, according to Zemplen, for the purpose of de-O-benzoylation, leads without difficulty to "GPA alcohol" (formula (8)) in yields of 90% or higher

We claim:

1. Derivatives of D-glucopyranosyl-alpha-(1→5)-D-arabinonic acid of the formula:

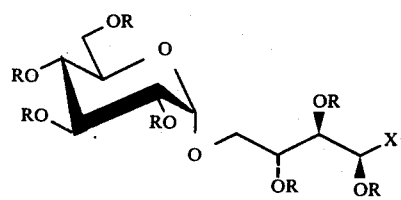

(I)

wherein X is a member selected from the group consisting of —COOM, —COOR', —CONH$_2$, and —CH$_2$OH, and M is an alkali metal and R' is an alkyl group having 1 to 20 carbon atoms; and wherein R is a hydrogen atom or an acyl group having 1 to 20 carbon atoms; the compounds of formula (I) including those aliphatic acid group is closed in a lactone ring represented by the formula:

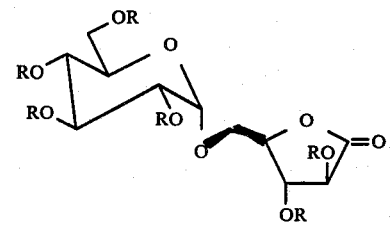

wherein R has the same meaning as set forth above.

2. A compound according to claim 1, wherein X is —CH$_2$OH and R is H; the resulting compound being D-glucopyranosyl-alpha-(1→5))-D-arabinitol, of the formula:

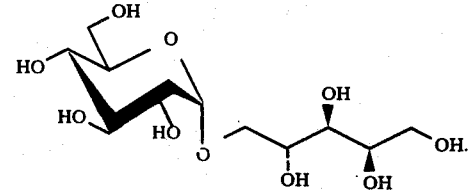

3. A compound according to claim 1, wherein X is —COOK and R is H; the resulting compound being D-glucopyranosyl-alpha—(1→5)-D-arabinonic acid potassium salt of the formula:

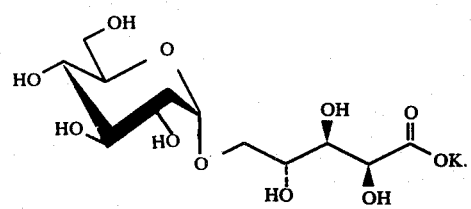

4. A compound according to claim 1, wherein X is —COOCH$_3$ and R is H; the resulting compound being D-glucopyranosyl-alpha-(1→5)-D-arabinonic acid methyl ester of the formula:

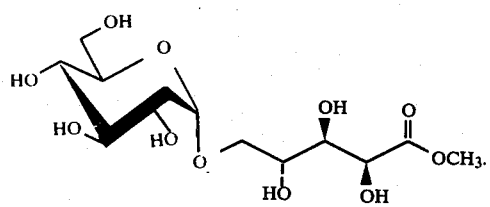

5. A compound according to claim 1, wherein X is —COOCH$_3$, and R is —COCH$_3$; the resulting compound being 2,3,4,6-tetra-O-acetyl-D-glucopyranosyl-alpha(1→5)-2,3,4-tri-O-acetyl-D-arabinonic acid methyl ester of the formula:

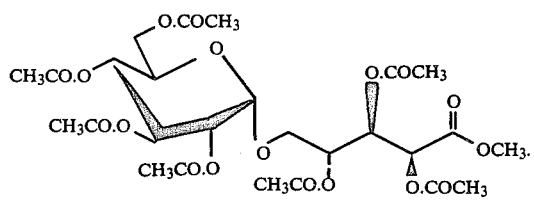

6. A compound according to claim 1, wherein X is —CONH₂ and R is H; the resulting compound being D-glucopyranosyl-alpha (1→5)-D-arabinonic acid amide of the formula:

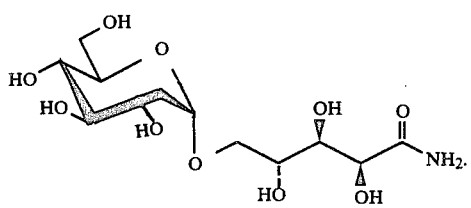

7. A compound according to claim 1, wherein the arabinonic acid is closed in a lactone ring and R is H; the resulting compound being D-glucopyranosyl-alpha(1→5)-D-arabinonic acid gamma-lactone, of the formula:

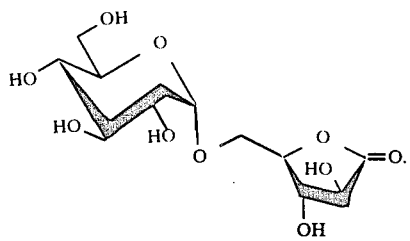

8. A compound according to claim 1, wherein the arabinonic ring is closed in a lactone ring and R is —COC₆H₅; the resulting compound being 5-O-(2,3,4,6-tetra-O-benzoyl-alpha-D-glucopyranosyl)-2,3-di-O-benzoyl-D-arabinonic acid gamma-lactone of the formula:

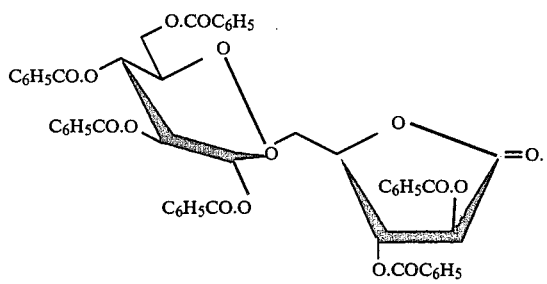

9. A compound according to claim 1, wherein X is —CH₂OCOC₆H₅ and R is —COC₆H₅, the resulting compound being the octabenzoate of D-glucopyranosyl-alpha(1→5)-D-arabinonic acid alcohol of the formula:

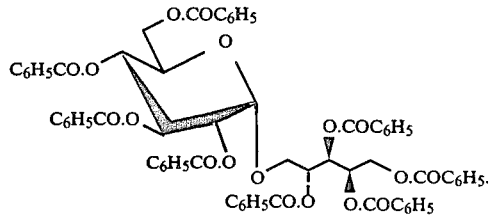

10. A process of preparing derivatives of D-glucopyranosyl-alpha(1→5)-D-arabinonic acid of the formula:

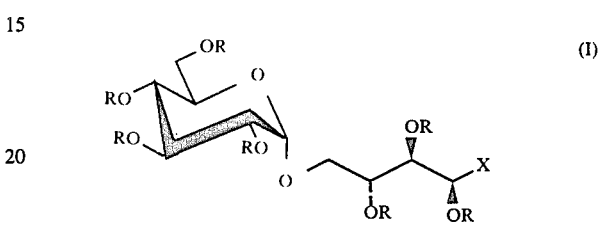

which comprises:
oxidizing isomaltulose in an alkali metal hydroxide with an oxygen containing gas, and
isolating the resulting salts from the reaction mixture by direct crystallization
thereby providing the alkali metal salt of D-glucopyranosyl-alpha(1→5)-D-arabinonic acid
wherein X is a member selected from the group consisting of —COOM, —COOR′, —CONH₂, and —CH₂, and M is an alkali metal and R′ is an alkyl group having 1 to 20 carbon atoms; and wherein R is a hydrogen atom or an acyl group having 1 to 20 carbon atoms,
the compounds of formula (I) including those in which the aliphatic group is closed in a lactone ring represented by the formula:

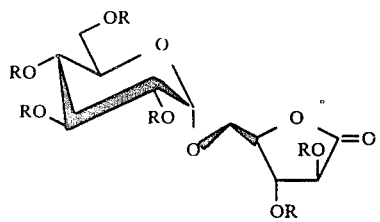

where R has the same meaning as set forth above.

11. The process of claim 10, wherein the alkali metal salt of the D-glucopyranosyl-alpha(1→5)-D-arabinonic acid is treated with an alkanol in the presence of an ion exchange medium, thereby providing the corresponding alkyl ester of D-glucopyranosyl-alpha(1→5)-D-arabinonic aicd.

12. The process of claim 10, wherein the alkali metal salt of D-glucopyranosyl-alpha(1→5)-D-arabinonic acid is treated with an acidic ion exchange medium is an aqueous solution, thereby providing the corresponding gamma-lactone of D-glucopyranosyl-alpha(1→5)-D-arabinonic acid.

13. The process of claim 11, wherein the alkyl ester of D-glucopyranosyl-alpha(1→5)-D-arabinonic acid is treated with anhydrous ammonia in methanol, thereby providing the corresponding D-glucopyranosyl-alpha(1→5)-D-arabinonic acid amide.

14. The process of claim 11, wherein one of the D-glucopyranosyl-alpha(1→5)-D-arabinonic acid alkyl ester and a heptaacylate of the D-glucopyranosyl-alpha(1→5)-D-arabinonic alkyl ester is reduced with one of a complex metal hydride and catalytically activated hydrogen, and the resulting D-glucopyranosyl-alpha(1→5)-D-arabinitol is then isolated by crystallization, thereby providing the corresponding D-glucopyranosyl-alpha(1→5)-D-arabinitol.

15. The process of claim 11, wherein the D-glucopyranosyl-alpha(1→5)-D-arabinonic acid alkyl ester is D-glucopyranosyl-alpha(1→5)-D-arabinonic acid methyl ester; and the D-glycopyranosyl-alpha(1→5)-D-arabinonic acid is methyl ester acetylated with acetic anhydride in an anhydrous solvent, thereby providing hepta-O-acetyl D-glucopyranosyl-alpha(1→5)-D-arabinonic acid methyl ester.

16. The process of claim 12, wherein one of the D-glucopyranosyl-alpha(1→5)-D-arabinonic acid gamma-lactone and a hexabenzoate of said D-glucopyranosyl-alpha(1→5)-D-arabinonic acid gamma lactone is reduced with one of a complex metal hydride and catalytically activated hydrogen, and the resulting D-glucopyranosyl-alpha(1→5)-D-arabinitol is then isolated by crystallization, thereby providing the corresponding D-glucopyranosyl-alpha(1→5)-D-arabinitol.

17. The process of claim 12, wherein the gamma lactone of D-glucopyranosyl-alpha(1→5)-D-arabinonic acid is benzoylated with benzoyl chloride in an anhydrous solvent, thereby providing hexa-O-benzoyl D-glucopyranosyl-alpha(1→5)-D-arabinonic gamma-lactone.

18. The process of claim 14, wherein the D-glucopyranosyl-alpha(1→5)-D-arabinitol is benzoylated with benzoyl chloride in an anhydrous solvent, thereby providing the octabenzoate of D-glucopyranosyl-alpha(1→5)-D-arabinitol.

19. The process of claim 16 wherein the D-glucopyranosyl-alpha(1→5)-D-arabinitol is benzoylated with benzoyl chloride, thereby providing the octabenzoate of D-glucopyranosyl-alpha(1→5)-D-arabinitol.

* * * * *